United States Patent
Blundred et al.

(10) Patent No.: US 10,322,234 B2
(45) Date of Patent: Jun. 18, 2019

(54) COVER BIASING MEANS FOR AN APPARATUS

(71) Applicant: Sanofi-Aventis Deutschland GMBH, Frankfurt am Main (DE)

(72) Inventors: Neal Alexander Blundred, South Coventry West Midlands (GB); Aled Meredydd James, Dorridge West Midlands (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 184 days.

(21) Appl. No.: 14/909,636

(22) PCT Filed: Aug. 4, 2014

(86) PCT No.: PCT/EP2014/066713
§ 371 (c)(1),
(2) Date: Feb. 2, 2016

(87) PCT Pub. No.: WO2015/018787
PCT Pub. Date: Feb. 12, 2015

(65) Prior Publication Data
US 2016/0184519 A1    Jun. 30, 2016

(30) Foreign Application Priority Data
Aug. 5, 2013 (EP) .................................... 13179301

(51) Int. Cl.
*A61M 5/19* (2006.01)
*A61M 5/20* (2006.01)
(Continued)

(52) U.S. Cl.
CPC .......... *A61M 5/19* (2013.01); *A61M 5/14244* (2013.01); *A61M 5/14566* (2013.01);
(Continued)

(58) Field of Classification Search
CPC ............ A61M 5/19; A61M 2005/2414; A61M 5/2448; A61M 2005/2496; A61M 5/20;
(Continued)

(56) References Cited

U.S. PATENT DOCUMENTS 2,118,221 A * 5/1938 Montuori ................ A61M 5/24
604/235
4,689,042 A * 8/1987 Sarnoff ............... A61M 5/2066
604/136
(Continued)

FOREIGN PATENT DOCUMENTS

DE    202009003009    6/2009
EP        2364741       9/2011
(Continued)

OTHER PUBLICATIONS

International Search Report and Written Opinion in International Application No. PCT/EP2014/066713, dated Nov. 3, 2014, 8 pages.
(Continued)

*Primary Examiner* — Bhisma Mehta
*Assistant Examiner* — Hong-Van N Trinh
(74) *Attorney, Agent, or Firm* — Fish & Richardson P.C.

(57) ABSTRACT

The invention relates to an Apparatus, especially a delivery device, comprising a housing (4100), a retainer (4200, 4200') for holding a cartridge (4220, 4220'), a cover part (4240, 4240') for accessing the retainer (4200, 4200'), the cover part (4240, 4240') being moveable relative to the housing (4100) between an open and a closed position, wherein the apparatus further comprises cover part biasing means for exerting a biasing force onto the cover part (4240, 4240') in the closed position to bias the cover part (4240, 4240') inwardly and/or distally against the housing (4100).

18 Claims, 13 Drawing Sheets

(51) Int. Cl.
*A61M 5/142* (2006.01)
*A61M 5/145* (2006.01)
*A61M 5/168* (2006.01)
*A61M 5/24* (2006.01)
*A61M 5/28* (2006.01)
*A61M 5/31* (2006.01)
*A61M 5/315* (2006.01)
*A61M 5/34* (2006.01)

(52) U.S. Cl.
CPC .......... *A61M 5/16827* (2013.01); *A61M 5/20* (2013.01); *A61M 5/2448* (2013.01); *A61M 5/284* (2013.01); *A61M 5/31* (2013.01); *A61M 5/2466* (2013.01); *A61M 5/31543* (2013.01); *A61M 5/345* (2013.01); *A61M 2005/2407* (2013.01); *A61M 2005/2474* (2013.01); *A61M 2005/2496* (2013.01); *A61M 2005/3104* (2013.01); *A61M 2005/3117* (2013.01); *A61M 2005/3125* (2013.01); *A61M 2005/3128* (2013.01); *A61M 2205/50* (2013.01); *A61M 2205/502* (2013.01)

(58) Field of Classification Search
CPC ................. A61M 5/2403; A61M 5/24; A61M 2005/2485
See application file for complete search history.

(56) References Cited

U.S. PATENT DOCUMENTS

| | | | |
|---|---|---|---|
| 7,967,784 B2* | 6/2011 | Pongpairochana | ..... A61M 5/20 604/134 |
| 2011/0202013 A1* | 8/2011 | Jeter | ..... A61M 5/002 604/228 |
| 2012/0056019 A1 | 3/2012 | Renz et al. | |
| 2012/0071819 A1* | 3/2012 | Bruggemann | .... A61M 5/14546 604/67 |

FOREIGN PATENT DOCUMENTS

| | | | | |
|---|---|---|---|---|
| GB | 2461732 | | 1/2010 | |
| GB | 2461732 A | * | 1/2010 | ............. A61M 5/24 |
| WO | WO2012/160156 | | 11/2012 | |

OTHER PUBLICATIONS

International Preliminary Report on Patentability in International Application No. PCT/EP2014/066713, dated Feb. 9, 2016, 5 pages.
Rote Liste, "50. Hypophysen-, Hypothalamushormone, andere regulatorische Peptide u. ihre Hemmstoffe," Chapter 50, ed. 2008, 20 pages.

* cited by examiner

COVER BIASING MEANS FOR AN APPARATUS

CROSS-REFERENCE TO RELATED APPLICATIONS

This application is a U.S. national stage application under 35 U.S.C. § 371of International Application No. PCT/EP2014/066713, filed on Aug. 4, 2014, which claims priority to European Patent Application No. 13179301.0, filed on Aug. 5, 2013, the entire contents of which are incorporated herein by reference.

The present patent application inter-alia relates to an apparatus, especially a delivery device, comprising a housing, a retainer for holding a cartridge and a cover part for accessing the retainer, the cover part being moveable relative to the housing between an open and a closed position. Such an apparatus may for example be used as a medical device, for example as a medicament delivery device, wherein the retainer of the apparatus for example contains at least one cartridge containing a drug to be delivered.

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

There is a general desire to improve dose accuracy of medicament delivery devices. The dose accuracy is inter alia dependent on the precise positioning of the cartridge containing the medicament within the device. A misalignment of the cartridge may for example cause a tilt or a displacement between the cartridge and a piston rod assembly for expelling the medicament from the cartridge. Therefore, retainers of medicament delivery devices in the state of the art often comprise a cartridge reference face to align the cartridge within the retainer.

It was observed, however, that regular handling of such a medicament delivery device by users may still cause misalignments of the cartridge within the retainer or of the retainer with respect to the chassis or housing of the medicament delivery device. For example, a squeezing force exerted on the cover part of the device may cause a cartridge to be tilted within the retainer or a retainer integral with the cover part to be displaced relative to the chassis or housing.

It is noted that the chassis is the device structure to which other parts of the device are fixed or attached. As also the housing is attached to the chassis, the terms chassis and housing may be used interchangeably in the following.

The precise control of drive train forces in order to expel a substance like a medicament from the cartridge is already challenging because the control must accommodate various factors. For example, a change in ambient temperature may alter the viscosity of the medicament considerably or it may change the sliding forces required to move a bung within the cartridge, and the drive train forces need to cope with the altered viscosity or sliding forces. Therefore, it is desirable to reduce factors that may influence the drive train forces—like an imprecise alignment of the cartridge within the retainer.

In light of the aforementioned, the invention inter-alia faces the technical problem of providing an apparatus, especially a medicament delivery device, which provides for better alignment of a cartridge in the retainer with respect to the housing.

This object is at least in part solved by an apparatus comprising a housing, a retainer for holding a cartridge, a cover part for accessing the retainer, the cover part being moveable relative to the housing between an open and a closed position, wherein the apparatus further comprises cover part biasing means for exerting a biasing force onto the cover part in the closed position to bias the cover part inwardly and/or distally against the housing.

In an example embodiment, the cover part and the retainer are combined in a single part, for example made from a single plastic material.

The apparatus may be a delivery device, especially a drug delivery device such as a medical device configured to eject a drug agent (e.g. a dose of a medicament) such as an infusion device or an injection device, for instance an insulin injection pen. Injection devices may be used either by medical personnel or by patients themselves. As an example, type-1 and type-2 diabetes may be treated by patients themselves by injection of insulin doses, for example once or several times per day.

In particular, the apparatus may be a medical device configured to deliver (e.g. eject) at least two drug agents from separate cartridges situated in two separate retainers.

Alternatively, the apparatus may for instance be configured to deliver (e.g. eject) a two-component adhesive from separate cartridges comprising a first component of the two-component adhesive (e.g. a binder) and a second component of the two-component adhesive (e.g. a hardener), respectively.

The apparatus comprises a cover part for accessing the retainer, wherein the cover part is moveable relative to the housing between an open and a closed position. The cover part may be connected to the housing by a joint. For example the cover may be pivotally connected to the housing by a hinge so that the cover part is pivotable between an open and a closed position. In the open position the cover part provides access to the retainer so that a cartridge may be inserted into the retainer or removed therefrom. In the closed position the cover part at least in part covers the retainer of the apparatus so that a cartridge is hindered from being inserted in or removed from the retainer. The cover part or an outside part thereof may be transparent to allow a cartridge such as a medicament cartridge within the retainer to be identified.

The apparatus comprises cover part biasing means for exerting a biasing force onto the cover part in the closed position to bias the cover part inwardly and/or distally against the housing.

Being in the closed position, cover parts usually still allow a residual movement due to plays and clearance fits of the housing or cover part geometry or in the joints between them. Therefore the position of the cover part relative to the housing may shift during regular use of an apparatus, so that a misalignment of the retainer or of a cartridge within the retainer may occur. For example, a person using the apparatus may exert a squeezing force onto the cover part of the apparatus, so that the cover part may show a displacement towards the inside of the housing.

This undesired displacement was found to be reducible or even preventable by providing cover part biasing means to bias the cover part inwardly and/or distally against the chassis/housing. The thus achieved bias of the cover part eliminates any slack between the cover part and the housing, so that the cover part rests in its relative position to the housing even if a user of the apparatus exerts a squeezing force onto the apparatus.

Biasing distally in this context is understood to mean that the respective part is biased towards a distal part of the housing, in particular in a basically longitudinal direction of the apparatus. For delivery devices, the term "distally" refers to the end of the device or a component of the device which is closest to the dispensing end of the device. Accordingly the term "proximally" refers to the end of the device or a component of the device which is furthest away from the dispensing end of the device.

Biasing inwardly in this context is understood to mean that the respective part is laterally biased towards the inside of the housing. For example, the cover part may be laterally biased against an inner face of the housing. For delivery devices, the term "laterally" refers to the directions basically perpendicular to the longitudinal axis between the proximal and distal end of the device.

The cover part biasing means may comprise a biasing member such as a spring, especially a coil spring, a leaf spring, a cantilever spring, or the like, or an elastic plastic or rubber element.

According to an embodiment of the apparatus the retainer is integral with the cover part. The retainer and the cover part are then functionally linked. Moving the cover part to an open position also moves the retainer relative to the housing of the apparatus. This integration is advantageous as it is space-saving and facilitates inserting and removing of cartridges.

According to an embodiment of the apparatus the cover part comprises a first hinge part and the housing comprises a second hinge part, the first and second hinge part forming a hinge to pivotally connect the cover part to the housing and the hinge comprising a clearance fit between the first and second hinge part, and the cover part biasing means are configured to exert a biasing force onto the cover part in the closed position to bias the first hinge part against the second hinge part.

The hinge may be a loose pin hinge, wherein for example the first hinge part is a ring and the second hinge part is a pin, wherein the outer diameter of the pin is smaller than the inner diameter of the ring. The cover part then hinges about the pin fixed within the housing. The loose pin hinge facilitates both manual and spring-triggered operation of the cover part. Especially, the loose pin hinge offers little resistance against opening (for example by a cover spring) or closing the cartridge holder (manually). As a consequence, a lower strength cover spring can be used. However, there is a compromise, namely a small amount of clearance that allows some minor movement of the closed cover part relative to the housing.

Because of the loose pin hinge there is a minor amount of clearance that allows the cover part to move slightly with respect to the housing or chassis. A movement of the cover part may likewise cause a movement of the retainer and therewith of a cartridge reference face of the retainer that is used to align a cartridge within the retainer. Such a movement is however undesirable because it requires a larger tolerance of the apparatus parts, for example of a piston rod assembly used to expel a substance from the cartridge within the retainer.

By providing cover part biasing means configured to exert a biasing force onto the cover part in the closed position to bias the first hinge part distally against the second hinge part, any slack, which the clearance of the hinge such as the loose pin hinge provides when the cover part is in the close position, may be reduced or even eliminated. In this way the effect of tolerances such as the hinge tolerances or the effect of a squeeze force on the position of the cover part, the retainer or a cartridge reference face of the retainer relative to the housing can be reduced or minimized.

According to an embodiment of the apparatus the apparatus comprises a cover latch for locking the cover part in the closed position, the cover latch being moveable relative to the cover part between a locked and an unlocked position, wherein the cover latch at least in part forms the cover part biasing means. Preferably, the cover latch is located within the apparatus, for example near the proximal end of the retainer and adjacent to a piston rod provided for expelling a substance from a cartridge in the retainer.

According to this embodiment the apparatus comprises a cover latch to lock the cover part. For example, a separate cover latch may be provided for each retainer of the apparatus.

The combination of the cover part biasing with the cover part latch functionality saves space and extra components within the device. The cover latch may for example be biased distally by a latch spring to exert a biasing force onto the cover part. Preferably, the cover latch has an outward-facing chamfer inclined at an oblique angle, which facilitates the manual closing of the cover against the force of the latch spring.

According to an embodiment of the apparatus the cover part comprises a locking extension with a locking head for interacting with the cover latch in the closed position of the cover part, the locking head comprising a first end configured to interact with an inclined surface of the cover latch in such a way, that in the closed position of the cover part and in the locked position of the cover latch the locking head is biased inwardly and/or distally against the chassis or housing. This embodiment combines the biasing of the cover part with the cover latch functionality thereby saving space and extra components within the device. The inclined surface may be formed as an inward-facing chamfer of the cover latch.

A further advantage of the inclined surface of the cover latch in combination with the first end of the locking head is that the cover latch may exert an assistive inward pull to the cover part as soon as the cover latch engages the locking head, especially before a switch for detection whether the cover is closed is triggered by the cover part. In this way, the cover latch exerts an inward pull causing the cover part to quickly close.

The locking extension with the locking head may in particular be arranged on an inner side wall of the cover part that is located between the cartridge retainer and the housing.

According to an embodiment of the apparatus the locking head comprises a second end configured to interact with an inclined surface of the housing in such a way that in the closed position of the cover part and in the locked position of the cover latch the cover part is biased inwardly and/or distally against the housing. The cover part is therewith biased against the housing to prevent relative movements between the cover part and the housing during operation. The inclined surface of the housing may be provided by a wedge-like part of the housing.

Preferably, the locking head of the cover part has the shape of a stepped extension forming the first and second end of the locking head. Especially, the first end may point proximally to interact with the cover latch and the second end may point laterally into the apparatus to interact with the inclined surface of the housing. The stepped profile of the stepped extension then provides a latching location for the cover latch and a biasing location for the housing, thereby defining axial and lateral limits for the cover part in the locked position.

Providing the locking head with a shape of a stepped extension invention separates the latching and biasing functionality and therefore makes the locking head geometry highly adaptable. Especially, the length of the extension as well as the step height and step length can be adapted at purpose. Thus, the locking head can be designed to extend to the desired location of the cover latch within the housing, so that the cover latch may be arranged more flexibly. Moreover, the locking head shape allows the angle of inclination of the inclined surface of the housing and/or of the cover latch and the position of both the cover latch and the inclined surface of the housing to be optimized (basically independently of the length of the inner side wall of the cover part) with reference to the hinge, with which the cover part is pivotally connected to the housing. Especially, these geometries may be optimized to distally and/or inwardly bias the cover part against a loose pin of a hinge provided on the housing to prevent the cover part from relative movement to the housing during operation.

By providing the locking head in the form of a stepped extension, the stepped extension may also be configured to mechanically trigger one or more operations of the apparatus during closing of the cover part, especially during an early phase of closing the cover part.

According to an embodiment of the apparatus the apparatus comprises a cover close switch for detecting whether the cover is in the closed position, the cover close switch being arranged to be activated by the locking head in the closed position of the cover part. The signal from the switch may for example be used to control the motor of the apparatus, especially to trigger the piston rod to advance towards the cartridge. Preferably, the locking head of the cover part and the cover close switch are arranged in such a way, that the cover close switch is triggered by the locking head when the cover part is in the closed position and abuts against the housing. For safe operation, further signals may be required to allow the motor to advance the piston rod towards the cartridge, such as a signal detecting the presence of the cartridge by a switch, optical detection means, and/or the like.

If the locking head has the shape of a stepped extension, it may also be configured to engage with the cover latch before the cover part is completely closed and abuts against the housing. Thereby, full engagement of the cover latch mechanism can be ensured prior to—for example—activation of a cover close switch by the cover part. This is advantageous over previous devices, in which a cover close switch might have been triggered before the cover part was fully locked by the cover latch.

According to an embodiment of the apparatus the retainer comprises a cartridge reference face for aligning a cartridge within the retainer, and the apparatus further comprises cartridge biasing means for exerting a biasing force onto a cartridge in the retainer to bias the cartridge against the cartridge reference face. The cartridge reference face serves as abutment feature against which the cartridge can be biased in order to align the cartridge within the retainer with high precision. In this way, the cartridge may be axially aligned within the retainer with respect to the cartridge reference face, so that the cartridge may be precisely positioned within the retainer. Furthermore, axial biasing of the cartridge in the retainer aids piercing of a cartridge septum by preventing the cartridge from unseating when presented with a needle by the user.

According to an embodiment of the apparatus the cartridge biasing means are separate from the cover part biasing means. If the cover latch for example forms the cover part biasing means, the cartridge biasing means are preferably separate from the cover latch. In particular, the cartridge biasing means and the cover part biasing means are moveable relative to each other.

In an apparatus, in which the cover latch and the cartridge bias are for example provided by a single component which is operatively coupled with the piston rod, the cartridge bias would push the cartridge axially against the cartridge reference face during operation and thereby also bias the retainer and the cover part. However, the direction of this push force is usually offset relative to the hinge connecting the cover part to the housing. Therefore, the cartridge bias may create a torque component that may cause the cover part to be pushed outward, leading to misalignment of the cover part and/or of the cartridge. By separating the cartridge biasing means and the cover biasing means, in particular the cover latch, the cover biasing means may be configured to counteract outward force components.

According to an embodiment of the apparatus the apparatus comprises a piston rod for expelling a substance from a cartridge within the cartridge holder and a cartridge bias sleeve slidably disposed over the piston rod, the cartridge bias sleeve being biased towards the cartridge reference face by sleeve bias means. The cartridge bias sleeve may bias the cartridge to position the cartridge in the retainer and align the piston rod relative thereto. Thus, the cartridge biasing sleeve acts as cartridge biasing means. Preferably, the cartridge bias sleeve is axially biased forward by a cartridge bias spring.

The cartridge biasing sleeve allows a precise positioning of a cartridge in the retainer and relative to the housing. For example, after a cartridge has been inserted into the retainer and after the cover part is in the closed position and latched, the cartridge may be in an initial general alignment within the retainer, but not yet biased against the cartridge reference face. Therefore, there may be some clearance between the cartridge and the retainer, and between the retainer and the piston rod assembly, which may lead to a cumulative clearance between the cartridge and the piston rod assembly. These tolerances may result in some slack or leeway which must be taken up by the piston rod assembly. By provision of the cartridge bias sleeve the cartridge can be biased to abut tightly against the cartridge reference face within the retainer. Furthermore, the retainer may be located precisely within the housing by biasing the cartridge and therewith the retainer itself.

A tight seating of the cartridge relative to the retainer and to the housing reduces the required tolerance of the piston rod assembly by increasing the seating precision of the cartridge within the retainer and within the chassis. This reduces, in turn, the required range of contact positions between the cartridge, especially a bung within the cartridge to expel a substance from the cartridge, and the piston rod. A reduction of the required range facilitates configuration of the piston rod to supply a consistent force to the cartridge bung more easily.

The cover latch provided as cover part biasing means may be slidably disposed adjacent to the cartridge bias sleeve. As noted above, the latch may be biased distally by a latch spring. It is an advantage that the latch spring is different from the cartridge bias spring, because this allows use of a softer latch spring while providing a strong cartridge bias spring.

According to an embodiment of the apparatus the piston rod comprises a protruding lip on the end of the piston rod facing the retainer and the cartridge bias sleeve comprises a corresponding rabbet on the end of the cartridge bias sleeve facing the retainer. The lip limits axial movement of the bias sleeve beyond the distal end of the piston rod. In this way the cartridge bias sleeve and the piston rod may be operatively coupled so that the cartridge biasing with the cartridge bias sleeve may be controlled by moving the piston rod.

According to an embodiment of the apparatus the cover latch is slidably disposed adjacent to the cartridge bias sleeve, wherein the cover latch comprises a keyway extending partway along the cover latch, the keyway engaging a corresponding lug provided on the cartridge bias sleeve. In this way the cover latch and the cartridge bias sleeve may be operatively coupled, so that especially the cover latch may be moved to an unlocked position by moving the cartridge bias sleeve. If in addition the cartridge bias sleeve is operatively coupled to the piston rod, the cover latch may be moved to an unlocked position by moving the piston rod.

The partway extension of the keyway allows the cover latch, when it is distally biased, to protrude beyond the distal end of the piston rod even though it may be axially restrained by the lug. The cover latch spring may therefore bias the cover latch distally against either the sleeve lug or the locking head of the cover part, so that the locking head need not extend to the piston rod. Therefore, the locking extension with the locking head may be designed to be spaced apart from the piston rod which facilitates opening and closing of the cover part.

By coupling the cover latch and the cartridge bias sleeve and/or the piston rod, it may also be ensured that the cartridge cannot be biased when the cover latch is unlocked and/or that the cover part is locked and properly closed prior to cartridge biasing. Moreover, this also allows the steps of closing the cover part, locking the cover latch and biasing the cartridge to be controlled by the apparatus only in dependence of the piston rod position, thereby reducing the number of components that must be controlled independently by the apparatus and thus the complexity of the controller.

According to an embodiment of the apparatus the cover part comprises an outer side wall covering the retainer to the outside, the outer side wall having resilient properties against a compressive force imposed from the outside. This may prevent direct transmission of forces onto the retainer and/or onto a cartridge within the retainer.

The resilient properties of the outer side wall of the cover may be provided by the material used for the outer side wall and/or by its geometric design. Providing resilient properties by the geometric design is advantageous in cases in which the choice of materials may be limited due to regulatory requirements, such as for medical devices, or design considerations. For example, the outer wall may extend from the distal end of the retainer substantially along the cartridge axis, tapering away from the cartridge axis thereby providing a clearance between the outer side wall and the cartridge in the retainer. The outer side wall then acts akin to a leaf spring and is able to pick up squeeze forces, thereby impeding direct transmission of these squeeze forces onto the cartridge. Although the transmission of squeeze forces may not be fully prevented, the outer side wall achieves that only residual forces are transferred onto the cartridge once the outer side wall is fully depressed. An additional advantage is that the outer side wall facilitates the design of a flush outer surface of the apparatus when the cover part is closed.

According to an embodiment of the apparatus, the apparatus comprises a first and a second retainer for each holding a cartridge, a first and a second cover part for accessing the first and second retainer, the first and second cover parts each being moveable relative to the housing between an open and a closed position, and a cover spring arranged such that the cover spring exerts an opening force both onto the first and onto the second cover part. In this way one cover spring may be used for exerting opening forces onto both the first and second cover part and an additional cover spring may be dispensed with, thereby reducing weight, construction complexity and costs. The cover spring may for example be arranged inside the apparatus in between the first and second cover part, for example adjacent to an inner side wall of the first and to an inner side wall of the second cover part.

Preferably, the apparatus is configured such that the first or second cover part is moveable to the open position only if the respective other cover part is in the closed position. The opening force exerted by the cover spring is a function of the cover spring compression, i.e. the ratio of the current cover spring length within the apparatus to the cover spring length in its relaxed state. When only one cover part associated to the cover spring may be opened at a time, the compression of the cover spring solely depends on the position of this cover part, for example on the opening angle if it is a hinged cover part. This embodiment has the advantage that a defined opening force is exerted on the cover part. If both cover parts could be opened at a time, the compression and therewith the respective opening forces would depend on the position of both cover parts and therefore be less well defined.

For example the apparatus may comprise a cover latch for each of the two cover parts which are constructed and/or controlled such that a cover latch of a cover part may only be unlocked if the respective other cover latch is locked and the respective other cover part is in the closed position.

According to an exemplary embodiment of the apparatus the apparatus is a medical device, especially a medicament delivery device, or part of a medical device. The precise positioning of a cartridge and/or of the retainer within the housing is especially important for medical devices, in which the cartridge may for example be a medicament containing cartridge. These devices require a precise and predictable operation to ensure a safe use of the devices. For example, in medicament delivery devices such as medical devices for ejecting a medicament, the dosage precision may depend on the positioning of the cartridge and/or of the retainer. A medical device with the features according to the embodiments described above therefore ensures a higher dosage precision.

According to an exemplary embodiment of the apparatus the apparatus is hand-held. Hand-held devices may be exposed to lateral squeezing forces or the like during handling by the user. A hand-held apparatus having the features of one of the embodiments described above ensures a more precise positioning of the cartridge or of the retainer within the housing even when exposed to squeezing forces, so that a precise operation of the apparatus, like ejection of a predetermined medicament dosage, is improved.

These as well as other advantages of various aspects of the present invention will become apparent to those of ordinary skill in the art by reading the following detailed description, with appropriate reference to the accompanying drawings, in which.

Figure 1:
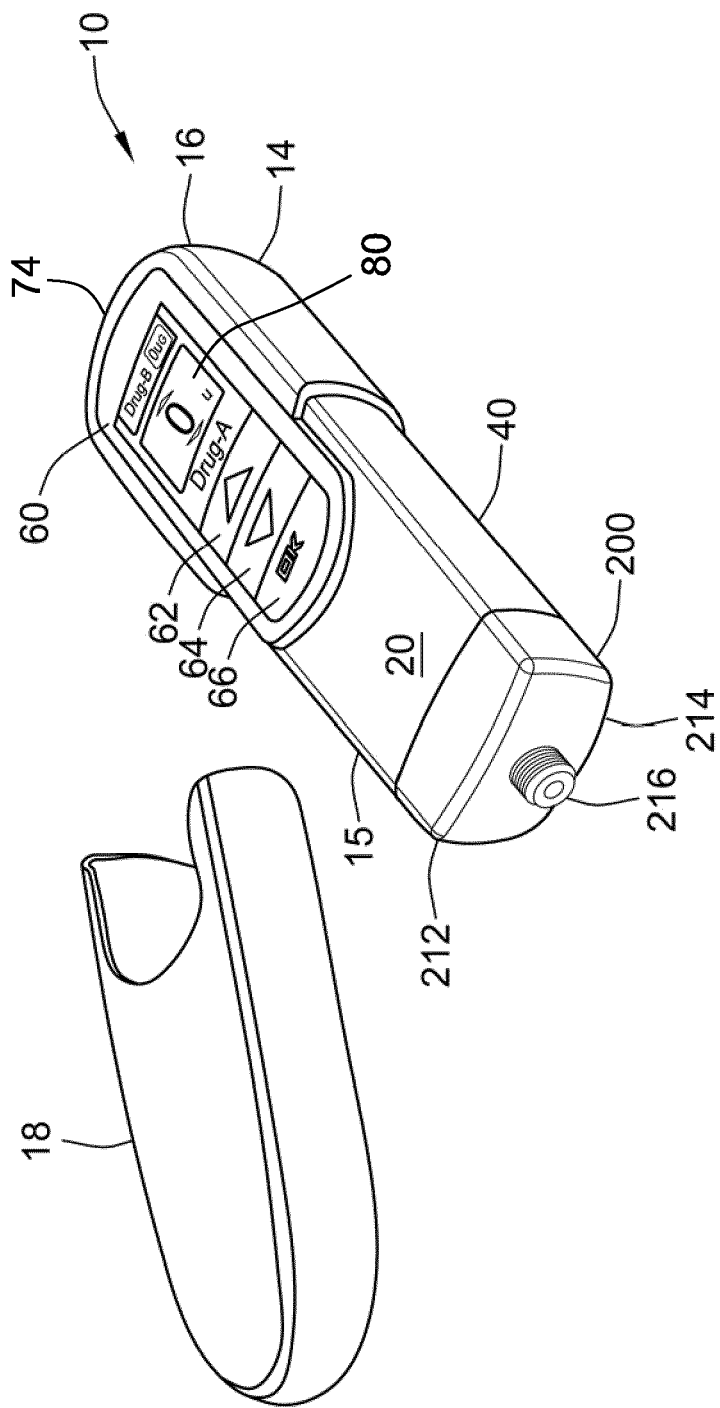
FIG. 1 illustrates a perspective view of a delivery device with an end cap of the device removed.
Figure 2:
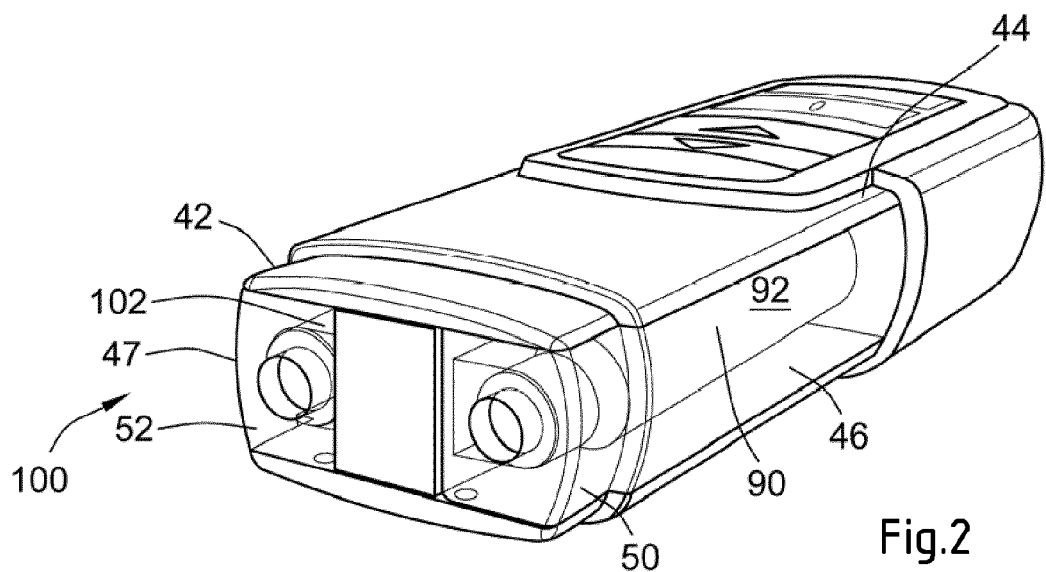
FIG. 2 illustrates a perspective view of the delivery device distal end showing the cartridge.
Figure 12A:
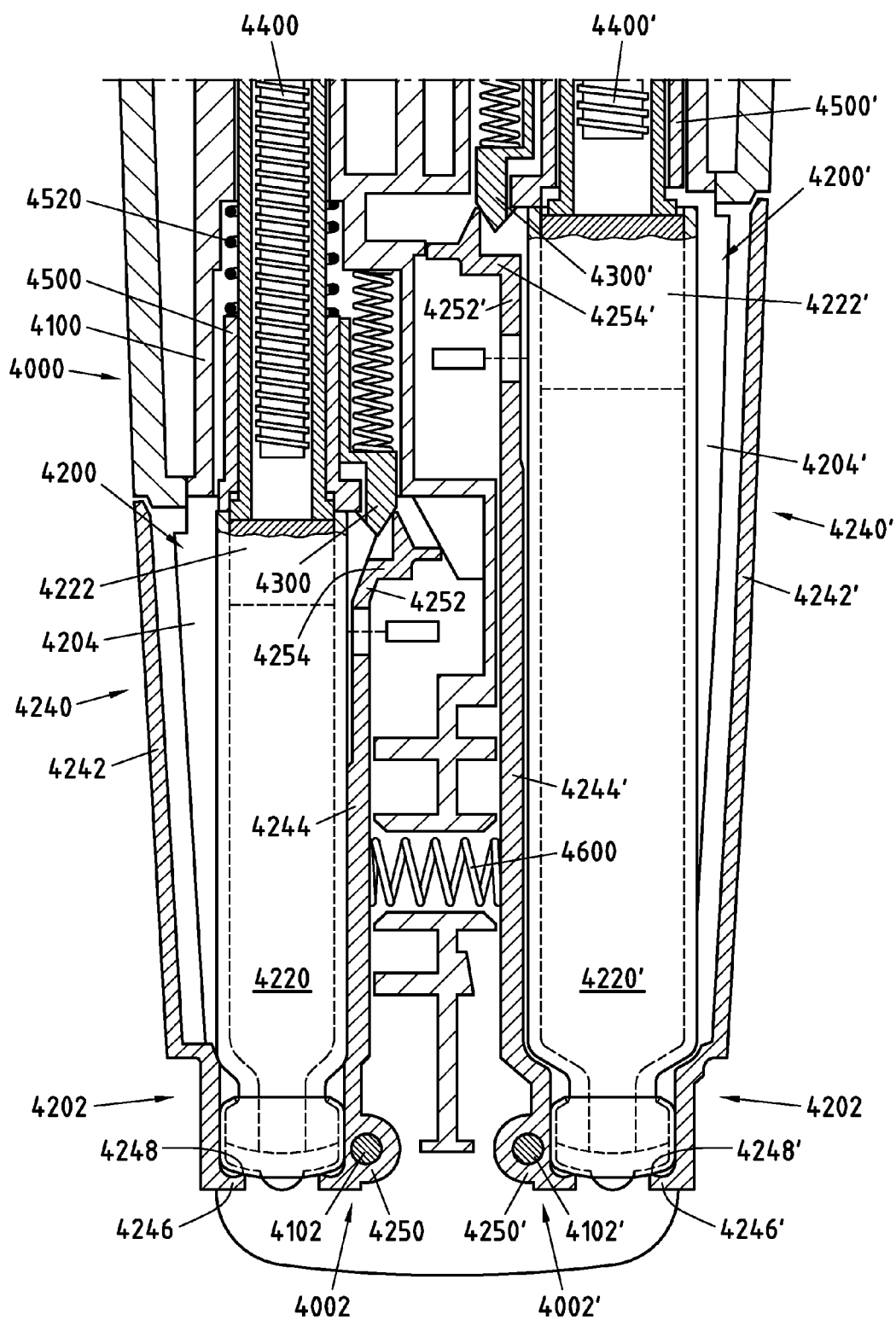
Figure 13A:
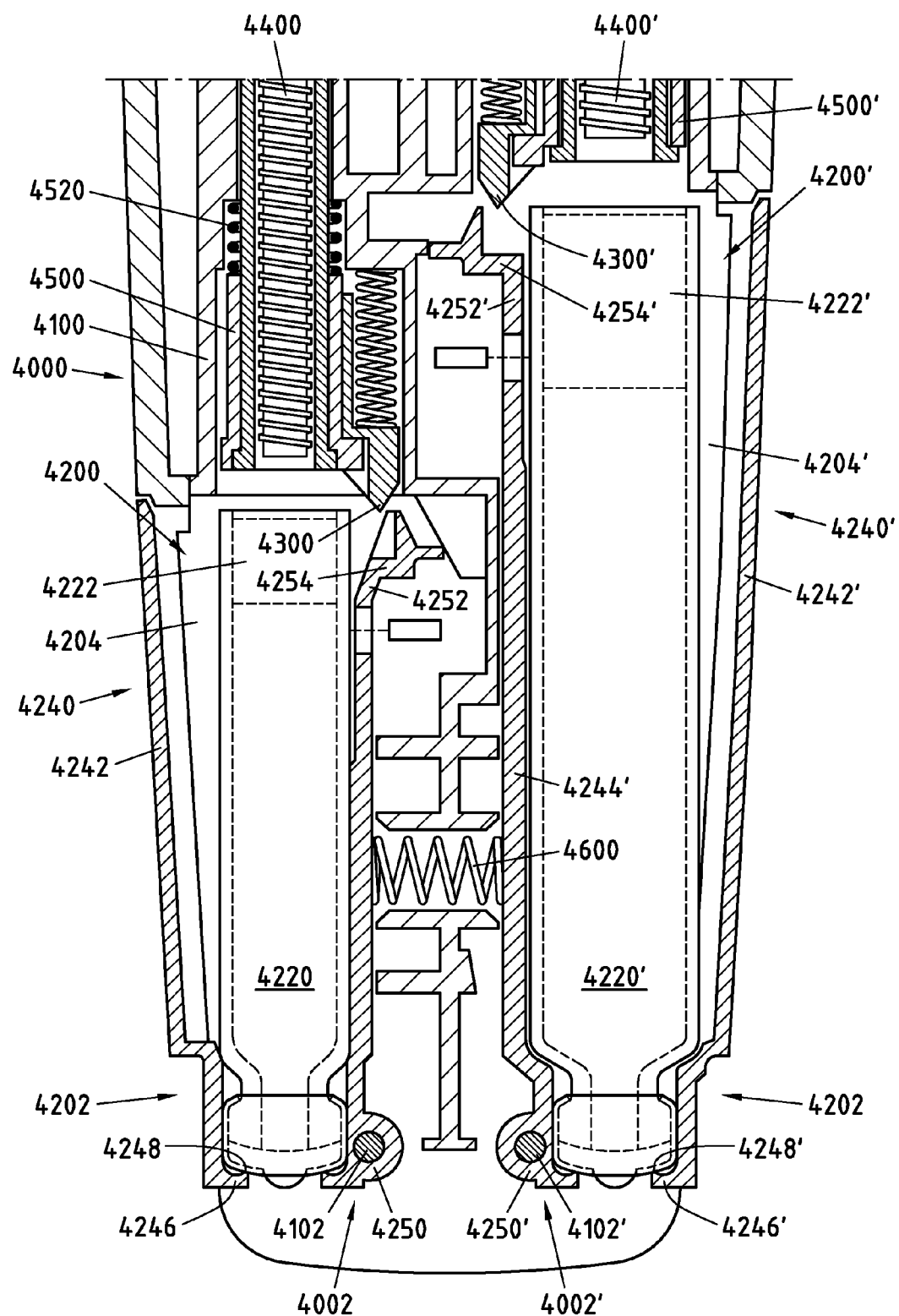
Figure 14A:
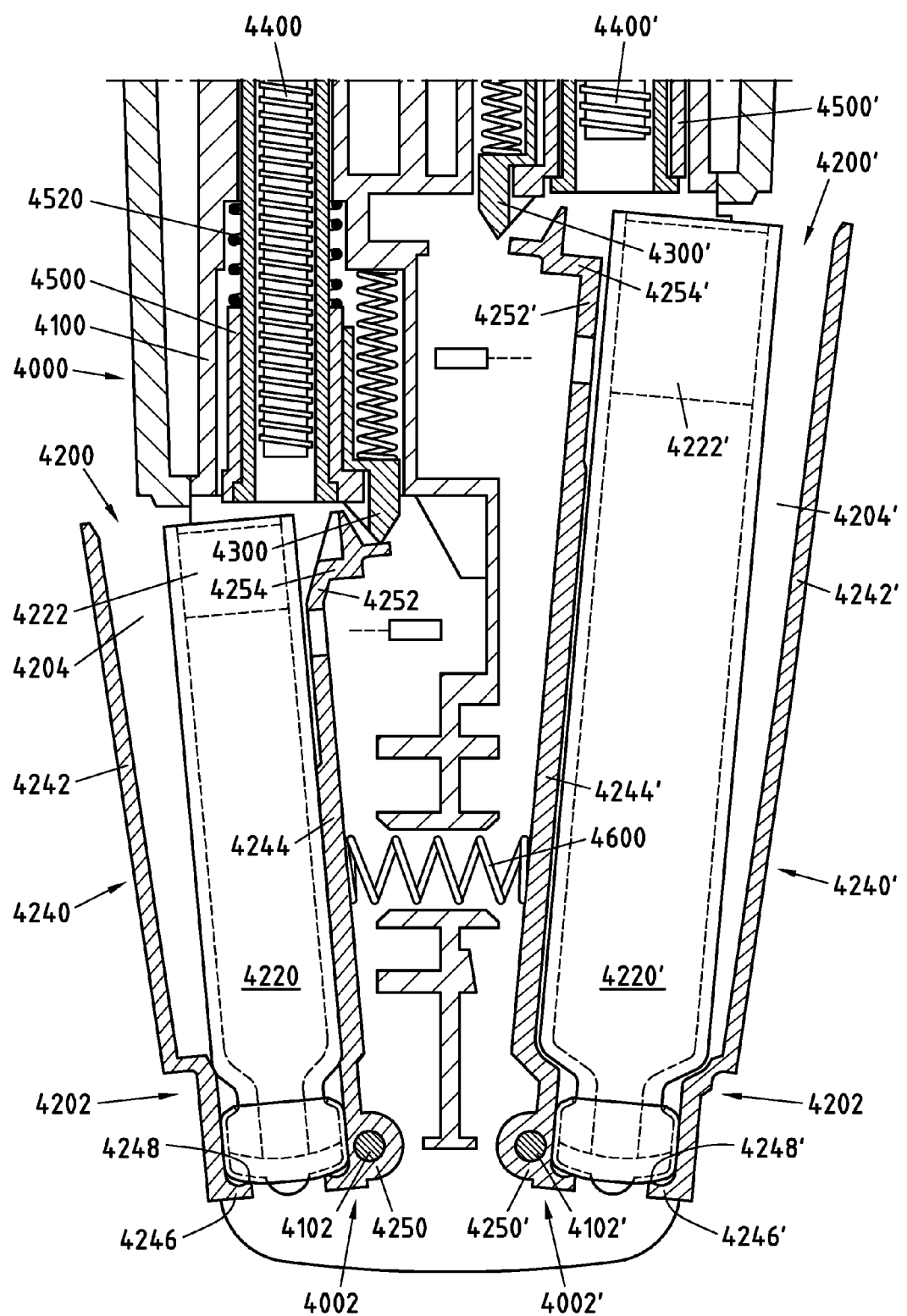
Figure 12B:
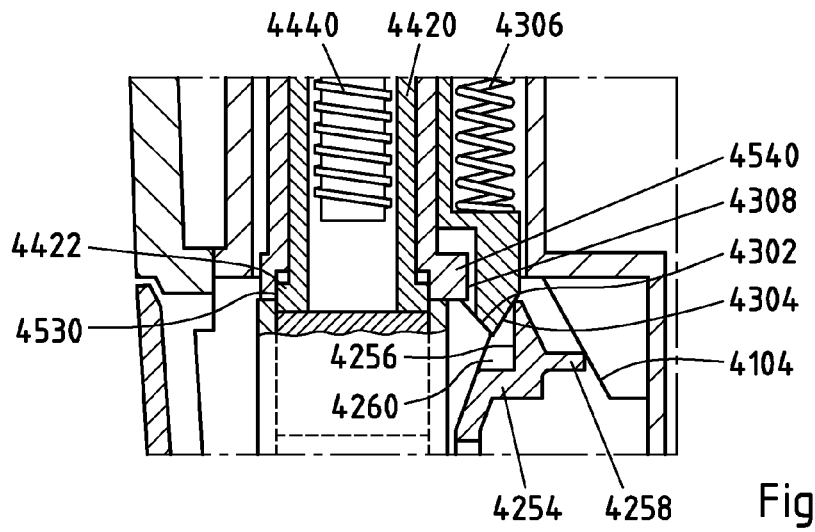
Figure 13B:
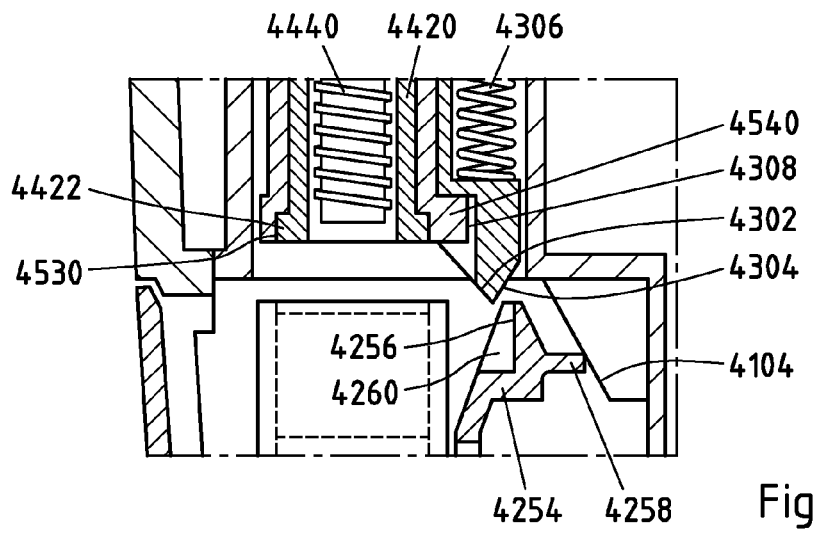
Figure 14B:
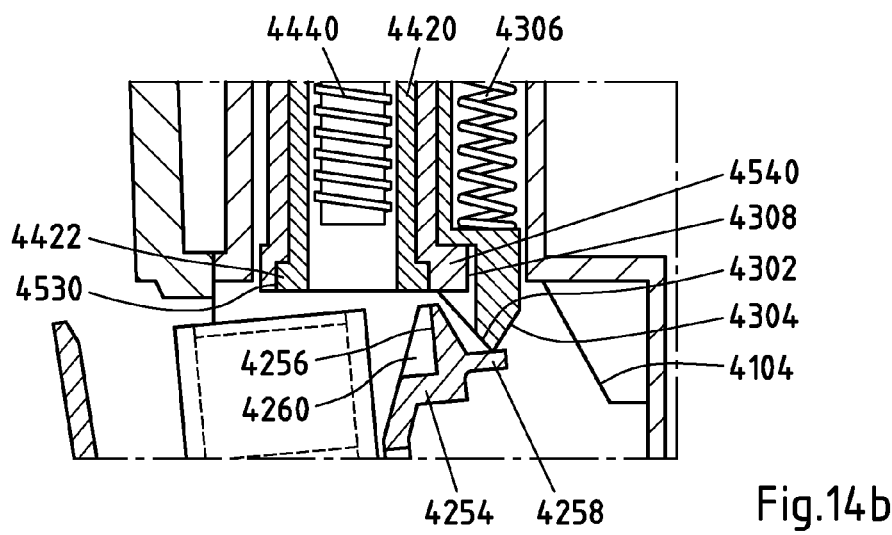

FIG. 12*a* illustrates a cross-sectional view of a cartridge holder for a delivery device as illustrated in FIG. 1 or 2 with two cartridge retainers being in a closed position and two cover latches being in a locked position;

FIG. 12*b* illustrates a detail of FIG. 12*a*;

FIG. 13*a* illustrates a cross-sectional view of the cartridge holder of FIG. 12*a* with the two cartridge retainers being in a closed position and the two cover latches being in an unlocked position;

FIG. 13*b* illustrates a detail of FIG. 13*a*;

FIG. 14*a* illustrates a cross-sectional view of the cartridge holder of FIG. 12*a* with the two cartridge retainers being in a partially open position; and FIG. 14*b* illustrates a detail of FIG. 14*a*.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1). The user interface of the drug delivery device may comprise additional buttons, such as a "menu" button, a "back" button, or a "light" button to switch on an illumination of the display.

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
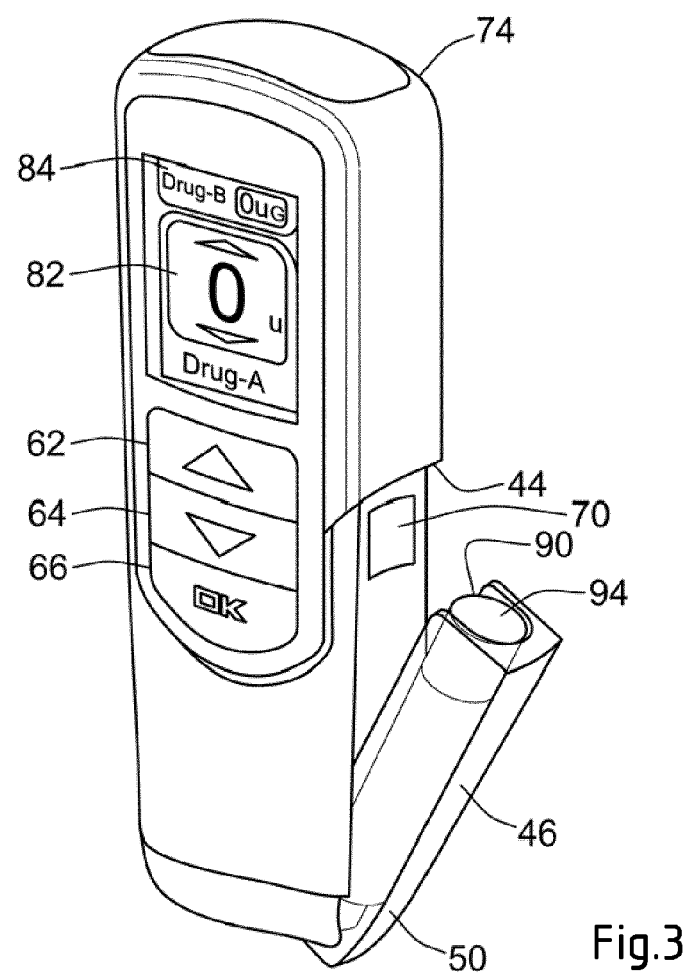
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
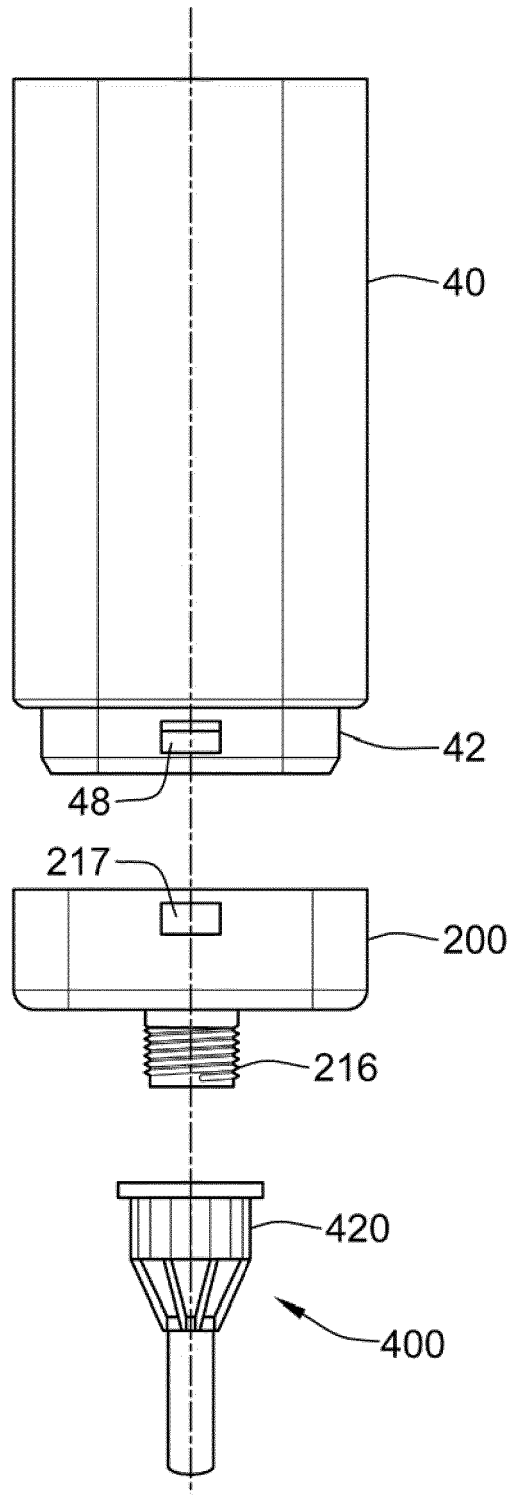
FIG. 4 illustrates a dispense interface and a dose dispenser that may be removably mounted on a distal end of the delivery device illustrated in FIG. 1.

As mentioned above when discussing FIG. 1, a dispense interface 200 can be coupled to the distal end of the cartridge holder 40. FIG. 4 illustrates a flat view of the dispense interface 200 unconnected to the distal end of the cartridge holder 40. A dose dispenser or needle assembly 400 that may be used with the interface 200 is also illustrated and is provided in a protective outer cap 420.

Figure 5:
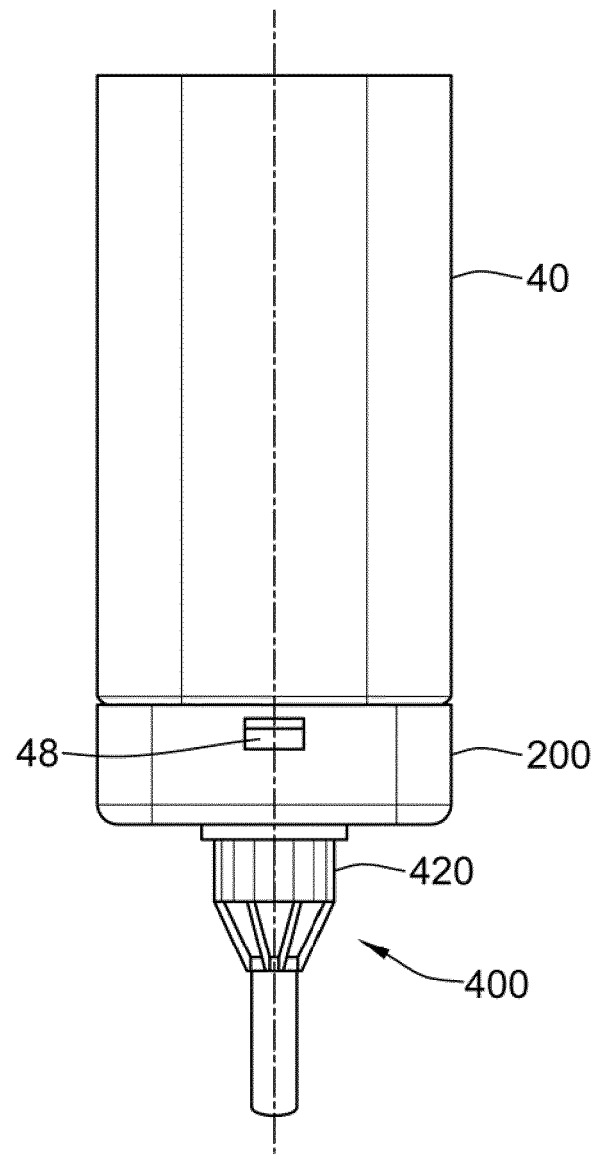
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means 48 between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
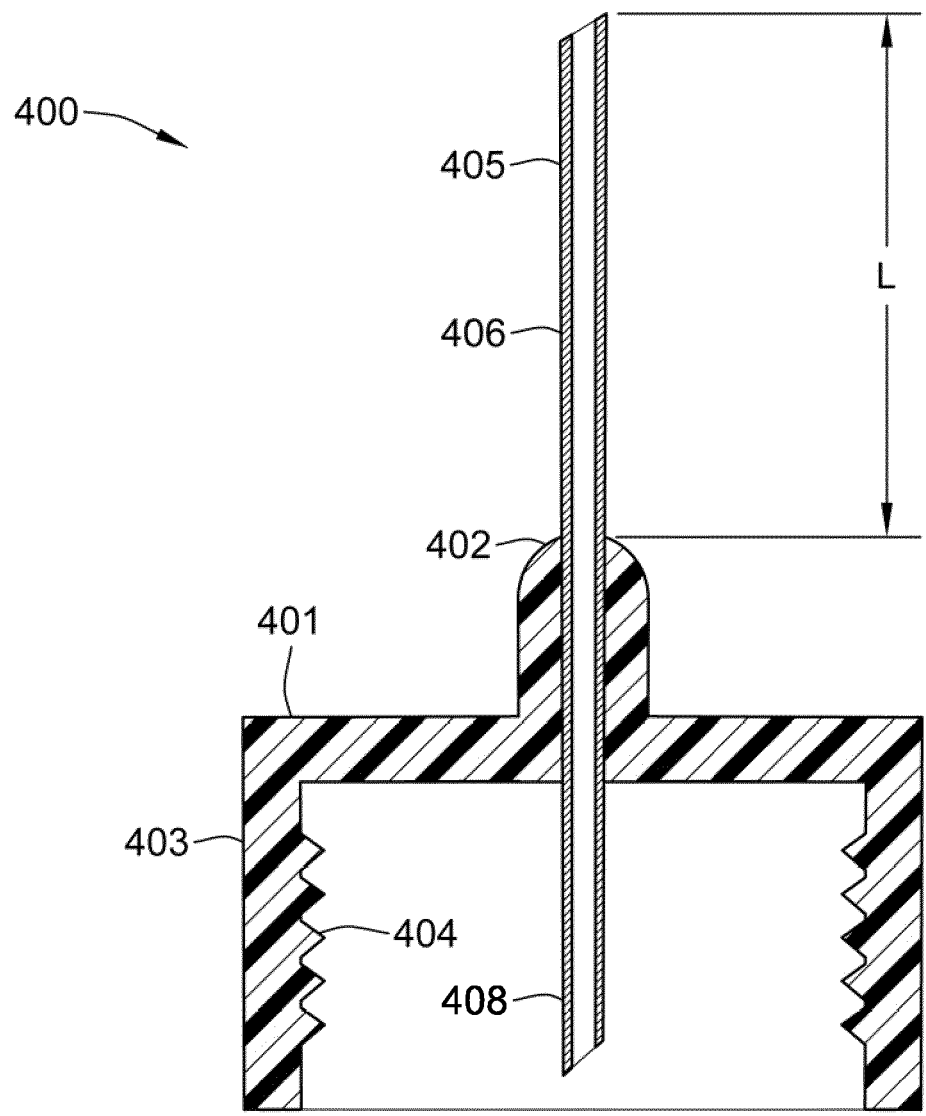
FIG. 6 illustrates one arrangement of a needle assembly that may be mounted on a distal end of the delivery device.
Figure 7:
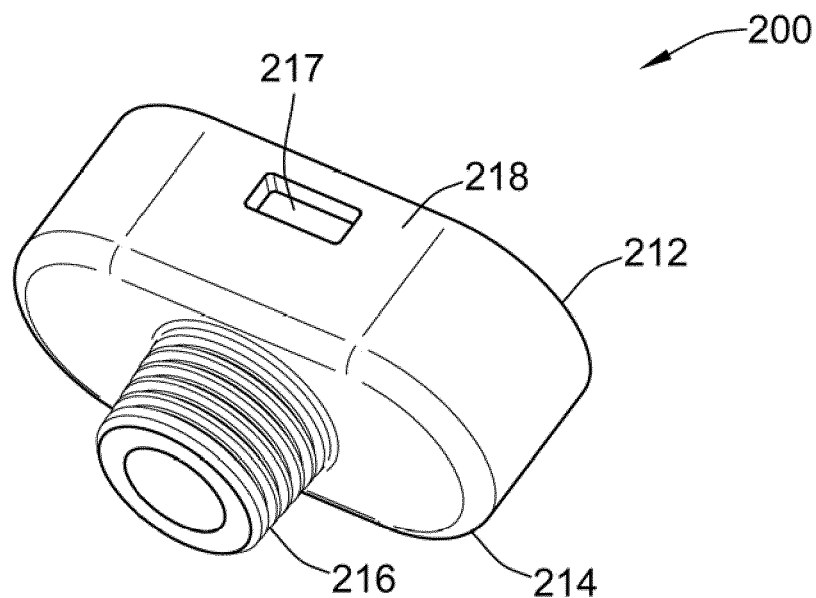
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 400 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 408 of the needle assembly 400 protrudes from an opposite side of the circular disc so that it is concentrically surrounded by the sleeve 403. In one needle assembly arrangement, the second or proximal piercing end 408 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:

a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
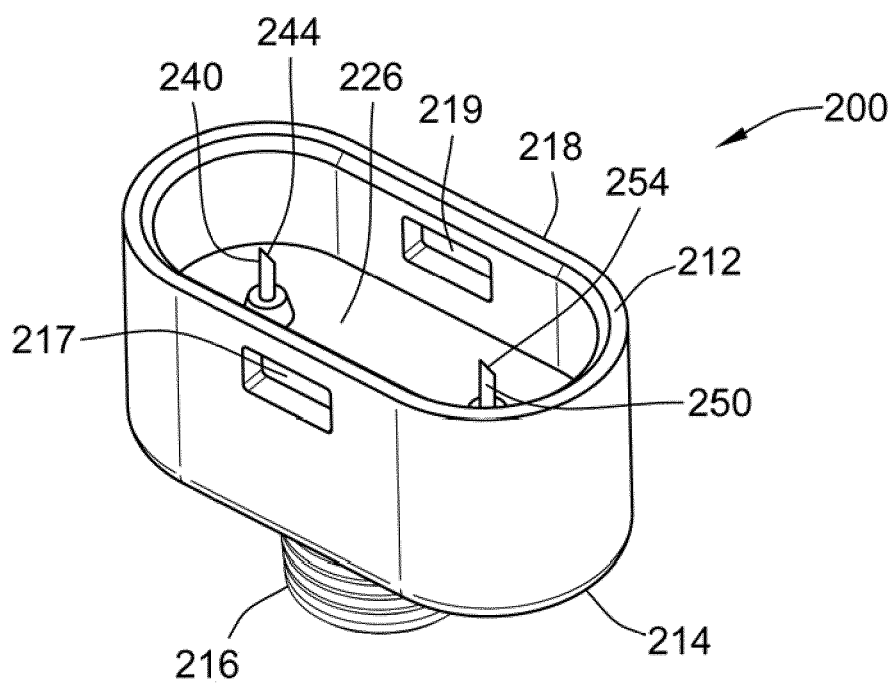
FIG. 8 illustrates another perspective view of the dispense interface illustrated in FIG. 4.
Figure 9:
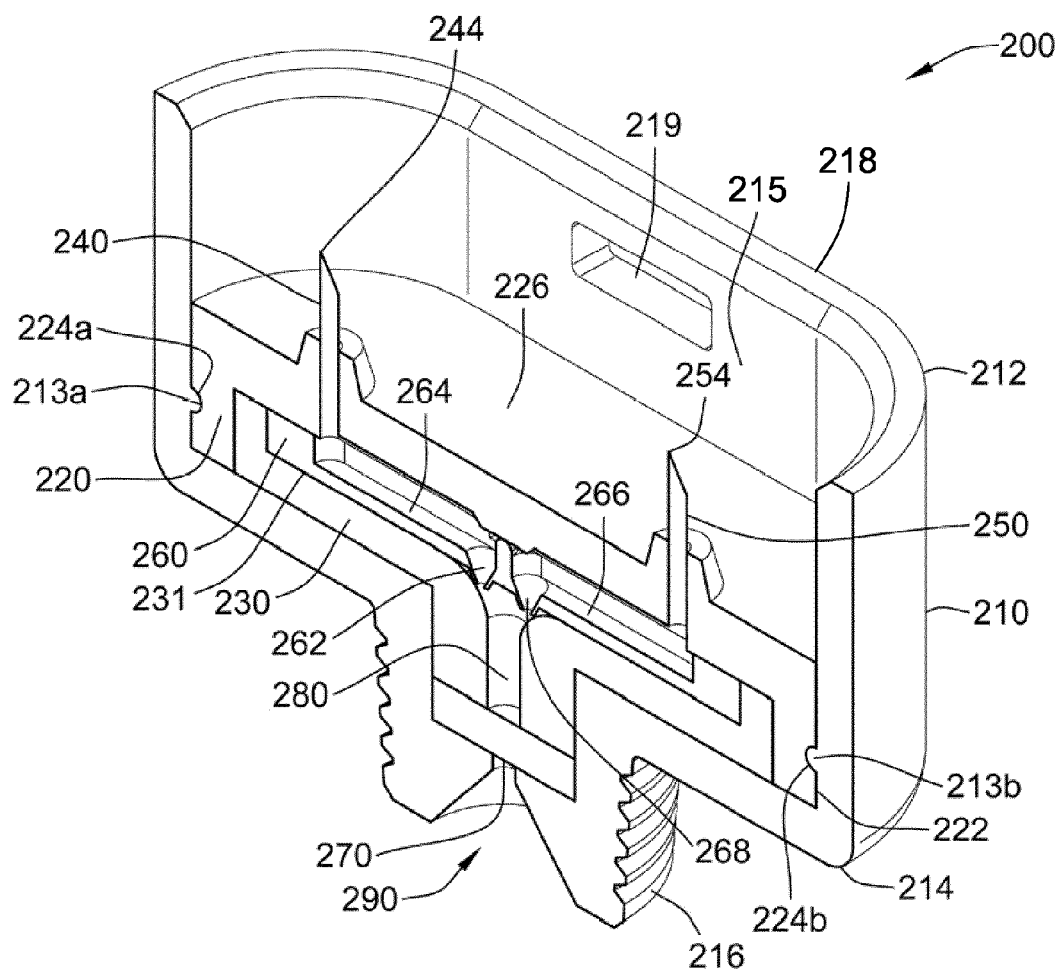
FIG. 9 illustrates a cross-sectional view of the dispense interface illustrated in FIG. 4.
Figure 10:
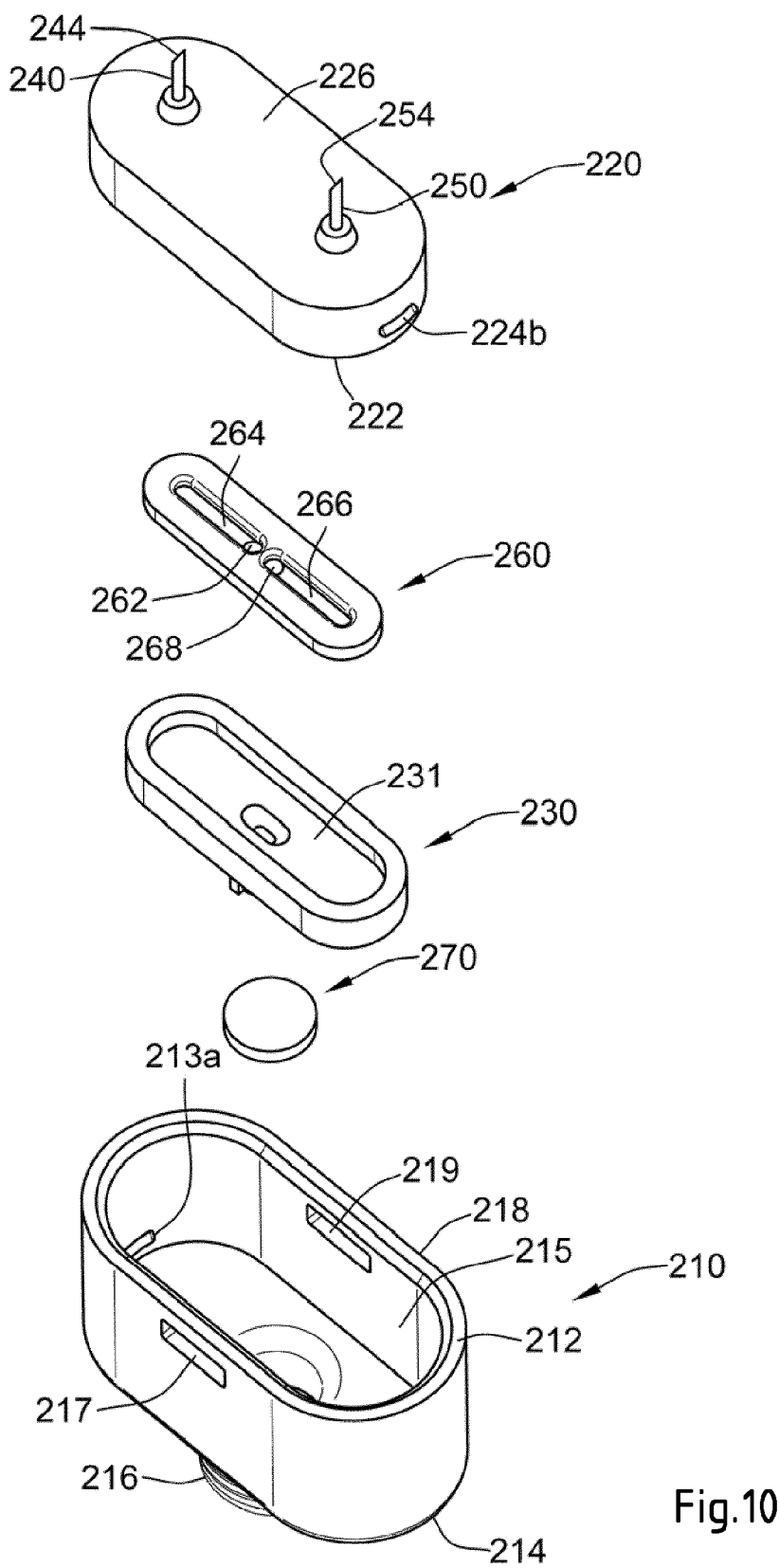
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
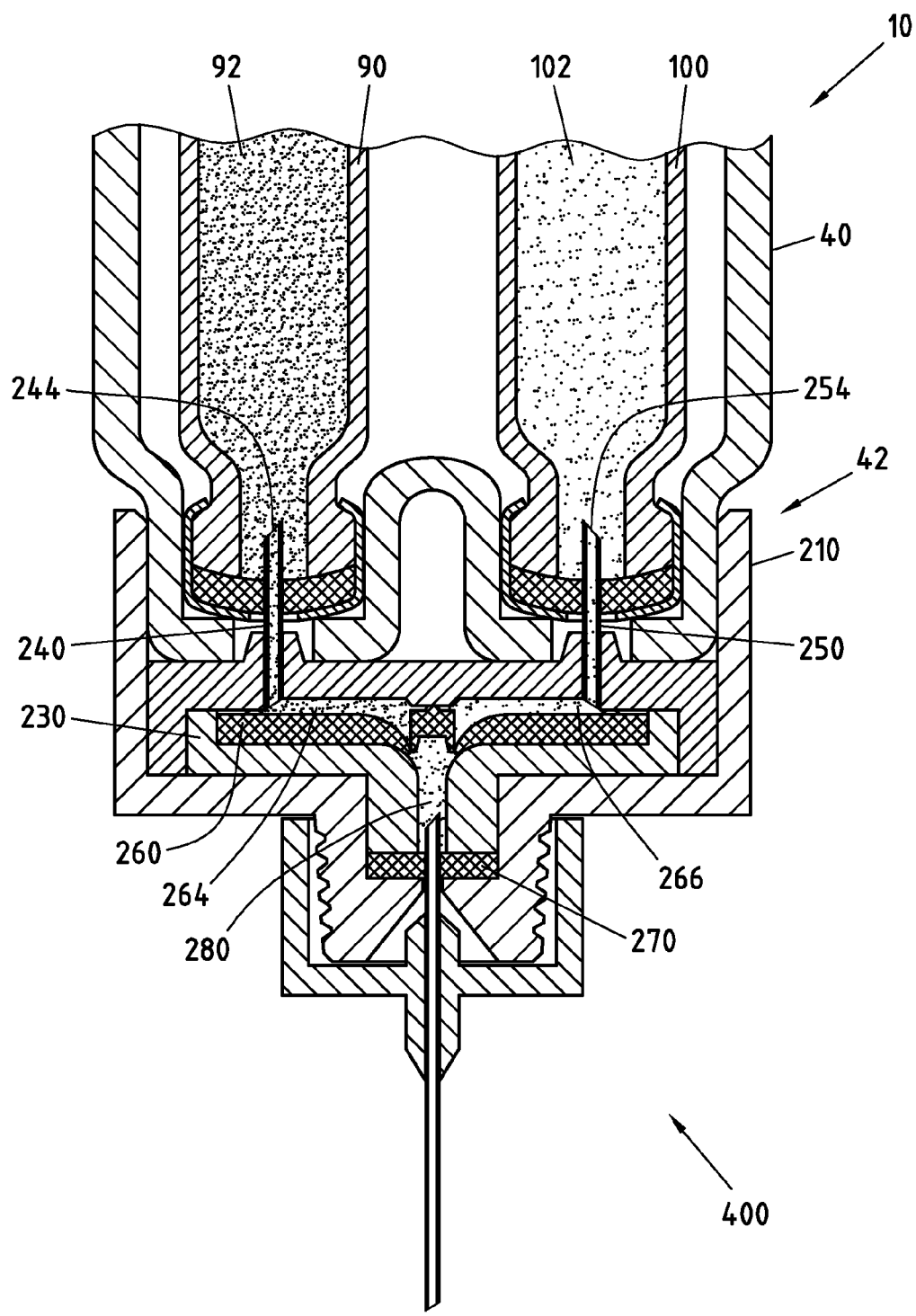
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

FIGS. 12a to 14b illustrate an embodiment of cartridge holder 4000 alternative to the embodiment of the cartridge holder 40 illustrated in FIGS. 1 to 5 and, basically, the differences are described only.

As will now be discussed in greater detail, in one preferred arrangement, the cartridge holder 4000 illustrated in FIGS. 12a to 14b inter alia comprises:
a. a housing or chassis 4100;
b. a first retainer 4200 for holding a first cartridge 4220;
c. a second retainer 4200' for holding a second cartridge 4220';
d. a first cover part 4240 for accessing the first retainer 4200;
e. a second cover part 4240' for accessing the second retainer 4200';
f. a first cover latch 4300 for locking the first cover part 4240 in a closed position;
g. a second cover latch 4300' for locking the second cover part 4240' in a closed position;
h. a first piston rod assembly 4400 for expelling a liquid from the first cartridge 4220;
i. a second piston rod assembly 4400' for expelling a liquid from the second cartridge 4220';
j. a first cartridge bias sleeve 4500 for biasing the first cartridge 4220;
k. a second cartridge bias sleeve 4500' for biasing the second cartridge 4220'; and
l. a cover spring 4600 for exerting an opening force onto the first cover part 4240 and the second cover part 4240'.

In the following, features of the cartridge holder 4000 will be described only for the respective first components (first retainer 4200, first cover latch 4300 etc.). However, the description applies accordingly for the respective second components (second retainer 4200', second cover latch 4300' etc.).

In the embodiment of the cartridge holder 4000 shown in FIG. 12a-14b the first retainer 4200 is formed integral with the first cover part 4240.

The first cover part 4240 comprises an outer side wall 4242 and an inner side wall 4244 with a head side wall 4246 in between. The head side wall 4246 forms a cartridge reference face 4248 to align the position of the first and second cartridge 4220 within cartridge retainer 4200.

The outer side wall 4242 extends from the distal end 4202 of the retainer 4200 substantially along the cartridge axis, tapering away from cartridge 4220, thereby providing a clearance 4204 between the outer side wall 4242 and the cartridge 4220 located in the retainer 4200. Due to this geometry, the outer side wall 4242 acts akin to a leaf spring and is able to pick up squeeze forces, thereby impeding direct transmission of these squeeze forces onto the cartridge 4220. The outer side wall 4242 therewith provides resilient properties due to its geometric design.

Cover part 4240 is pivotally connected to the housing/chassis 4100 by a loose pin hinge 4002, the loose pin hinge 4002 comprising a pin 4102 provided by the housing 4100 and a ring 4250 provided by cover part 4240. The outer diameter of pin 4102 is smaller than the inner diameter of ring 4250, so that there is a small clearance between pin 4102 and ring 4250 forming a clearance fit. Cover part 4240 is pivotable around loose pin hinge 4002 between a closed position as shown in FIGS. 12a and 13a and an open position as shown in FIG. 14a. This rotation is facilitated by the clearance in loose pin hinge 4002.

The inner side wall 4244 of cover part 4240 comprises a locking extension 4252 with a locking head 4254 for interaction with the first cover latch 4300. The locking head 4254 has the form of a stepped extension with a first end 4256 for interaction with the first cover latch 4300 and a second end 4258 for interaction with an inclined surface 4104 of the housing 4100. The locking head 4254 further comprises a recess 4260 into which the cover latch 4300 engages in its locked position to lock cover part 4240 as illustrated in FIGS. 12*a-b*.

The cover latch 4300 is moveable between a locked position illustrated in FIG. 12*b* and an unlocked position illustrated in FIG. 13*b* and is distally biased towards the locked position by a cover latch spring 4306. At its distal end, cover latch 4300 comprises an outward-facing chamfer 4302 and an inward-facing chamfer 4304 for interaction with the first end 4256 of locking head 4254. When closing cover part 4240, cover latch 4300 is then lifted by the interaction of first end 4256 with outward-facing chamfer 4302. Moreover, cover part 4240 is distally biased in the closed position due to interaction of first end 4256 with inward-facing chamfer 4304 and of second end 4258 with inclined surface 4104 of housing 4100. Thus, cover latch 4300 with inward-facing chamfer 4304 and cover latch spring 4306 act together as cover part biasing means.

The piston rod assembly 4400 comprises a hollow piston rod 4420 with a drive train 4440 inside, wherein drive train 4440 can be actuated by a drive train motor (not shown) to move piston rod 4420 along its longitudinal axes between different positions. For example FIG. 12*b* illustrates an armed position of piston rod 4420, in which it is located just above the bung 4222 of cartridge 4220. From this position, piston rod 4420 may be driven into cartridge 4220 to advance bung 4222 and therewith expel a medicament from cartridge 4220. FIG. 13*b* instead illustrates a retracted position of piston rod 4420, in which the piston rod 4420 has been retracted from cartridge 4220.

The first cartridge bias sleeve 4500 is slidably disposed over piston rod 4420 and is distally biased towards the cartridge 4220 by sleeve spring 4520. When piston rod 4420 is in the armed position or protrudes into cartridge 4220, sleeve spring 4520 distally biases the side of cartridge 4220 facing the cartridge biasing sleeve 4500 and thus biases cartridge 4220 against cartridge reference face 4248 thereby aligning cartridge 4220 within the retainer 4200. Thus, first cartridge bias sleeve 4500 and sleeve spring 4520 act together as cartridge biasing means for cartridge 4220.

Cartridge bias sleeve 4500 comprises a rabbet 4530 on its distal end facing retainer 4200, which is assigned to a corresponding protruding lip 4422 on the distal end of the piston rod 4420 facing retainer 4200. The lip 4422 limits axial movement of the cartridge biasing sleeve 4500 beyond the distal end of piston rod 4420. When piston rod 4420 is moved into the retracted position, sleeve spring 4520 is therefore likewise retracted, thereby releasing cartridge 4220.

The cartridge bias sleeve 4500 comprises a lug 4540 which engages with a corresponding keyway 4308 of cover latch 4300, so that when piston rod 4420 and cartridge bias sleeve 4500 are retracted as illustrated in FIG. 13*b*, cover latch 4300 is retracted as well and releases cover part 4240. The partway extension of keyway 4308 allows the cover latch 4300, when it is distally biased, to protrude beyond the distal end of piston rod 4420 even though it is axially restrained by the lug 4540.

The interactions between the individual components of cartridge holder 4000 during operation will be described in the following.

When at first no cartridge is provided in the retainer 4200, the piston rod 4420 is retracted to the armed position as illustrated in FIG. 14*a*. The armed position is not a fully retracted position, but allows the cover latch 4300 to engage with cover part 4240 during closing. The cartridge bias sleeve 4500 is biased distally by the cartridge bias spring 4520, but is also axially restrained by the lip 4422 of the piston rod 4420 leaving enough space to insert a cartridge 4220 into the cartridge holder 4000 and closing the cover part 4240.

Once cartridge 4220 has been inserted into the cartridge holder 4000 and the cover part 4240 is being closed, the first end 4256 of locking head 4254 interacts with the outward-facing chamfer 4302 of cover latch 4300 and pushes upward the cover latch 4300, so that cover latch 4300 eventually snaps back into recess 4260 thereby locking the cover part 4240 as illustrated in FIG. 12*a*.

When the cover part 4240 is locked, the inward-facing chamfer 4304 of cover latch 4300 and the inclined surface 4104 of housing 4100 engage with locking head 4254, thereby biasing the cover part 4240 and therewith the cartridge reference face 4248 distally against the housing 4100 so that the cartridge reference face 4248 is properly aligned relative to the housing 4100 before the cartridge 4220 is biased against the cartridge reference face 4248 by the cartridge bias sleeve 4500.

Once the cover part 4240 is latched, the motor control (triggered for example by a door close switch and/or a cartridge detection switch or sensor) advances the piston rod 4420. Thereby, cartridge bias sleeve 4500, which is urged against lip 4422, slides distally along with the piston rod 4420 until the cartridge bias sleeve 4500 abuts against the proximal end of cartridge 4220. Further advancement of piston rod 4420 into the cartridge 4220 de-keys the lip 4422 from sleeve rabbet 4530. In this way, sleeve 4500 pushes the cartridge 4220 against the cartridge reference face 4248 of retainer 4200 and aligns the cartridge 4220 within the retainer 4200.

Conversely, when the cartridge 4220 shall be taken out of retainer 4200 and for example be replaced by a new cartridge, the cartridge 4220 may be released and the cover part 4240 unlatched by retracting piston rod 4420 to its fully retracted position as illustrated in FIGS. 13*a-b*, i.e. beyond its respective armed position. This is advantageous because the full piston rod retraction and therewith the automatic release of cartridge 4220 and unlatching of cover part 4240 may be easily controlled, for example by a separate cover open button or switch.

When piston rod 4420 is retracting to its fully retracted position, it pulls proximally the cartridge bias sleeve 4500 and releases cartridge 4220 from the distal biasing. Furthermore, the retraction of cartridge bias sleeve 4500 causes the sleeve lug 4540 to abut the end of the keyway 4308, thereby pulling the cover latch 4300 distally, which in turn allows the cover latch 4300 to disengage from the stepped extension 4252.

Once unlatched, the cover part 4240 is pushed open by cover spring 4600. The piston rod 4420 then may immediately return from its fully retracted position to its armed position, in which the cover latch 4300 is ready to operate again.

FIGS. 13*a* and 14*a* show simultaneous unlocking of first and second cover latches 4300 and 4300' and simultaneous opening of first and second cover part 4240 and 4240', respectively. In such a situation, the opening force of cover spring 4600 exerted on cover parts 4240, 4240' depends on the opening angles of both cover parts 4240, 4240'.

In another embodiment of the cartridge holder 4000 the cartridge holder 4000 is configured such that the first cover part 4240 may only be opened when the second cover part 4240' is closed and vice versa. For example, the first cover latch 4300 may be constructed or controlled in such a way that it may be unlocked only if the second cover latch 4300' is locked and the second cover part 4240' is in a closed position, and the second cover latch 4300' may be constructed or controlled in such a way that it may be unlocked only if the first cover latch 4300 is locked and the first cover part 4240 is in a closed position. For this embodiment, the opening force of cover spring 4600 exerted on either the first or second cover part 4240, 4240' then only depends on the opening angle of the respective cover part and is therefore precisely defined.

A basic operational sequence of the cartridge latch 4300 of opening and closing the cover part 4240 will now be illustrated with reference to FIGS. 12b to 14b:

FIG. 12b first shows a detail of the initial condition of the cartridge holder 4000 with cover part 4240 being in a closed position and cover latch 4300 being in a locked position. The cover latch 4300 sits within a recess 4260 provided in the locking head 4254 of cover part 4240, preventing the cover part 4240 from opening. The piston rod 4420 is extended into the cartridge 4220 and the cartridge 4220 is biased against cartridge reference face 4246 by the cartridge bias sleeve 4500. The inclined surface 4104 of the housing 4100 clamps the locking head 4252 in cooperation with the inward-facing chamfer 4304 of cover latch 4300.

As the piston rod 4420 withdraws, due to the keying between the cartridge bias sleeve 4500 and the cover latch 4300 by keyway 4308 and lug 4540, the cover latch 4300 is withdrawn from the recess 4260, freeing the cover part 4240. A corresponding detail view of the cartridge holder 4000 with cover part 4240 being in a closed position and cover latch 4300 being in an unlocked position is shown in FIG. 13b.

The cover part 4240 is then opened by the cover spring 4600, which allows the cartridge 4220 to be removed. After the cover part 4240 has opened, the piston rod 4420 is advanced to the armed position which is equivalent to the position of FIG. 12b. A corresponding detail view of the cartridge holder 4000 with cover part 4240 being in an open position and cover latch 4300 being in a locked position is shown in FIG. 14b.

When cover part 4240 is closed again, locking head 4254 of cover part 4240 acts against cover latch 4300. Due to the inclined surface of the outward-facing chamfer 4302 of cover latch 4300, cover latch 4300 is forced upwards into the housing (to a similar position as in FIG. 13b) against the force of the cover latch spring 4306 and pops into recess 4260 of the locking head 4254. Cover part 4240 and cover latch 4300 are then again in the position shown in FIG. 12b. Only when the cover latch 4300 has engaged the recess 4260 of the cover head 4254, a switch is activated, which indicates that the cover is closed.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta⁻decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2, H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. An apparatus comprising:
a housing,
a first retainer for holding a first cartridge and a second retainer for holding a second cartridge,
a first cover part for accessing the first retainer and a second cover part for accessing the second retainer, the first and second cover parts being moveable relative to the housing between an open and a closed position,
a cover part biasing mechanism configured to exert a biasing force onto the first cover part in the closed position to bias the first cover part inwardly and/or distally against the housing, the cover part biasing mechanism comprising a cover latch being moveable relative to the first cover part, the cover latch configured to be deflected by the first cover part in the closed position, wherein deflection of the cover latch by the first cover part exerts the biasing force onto the first cover part, and
a cover spring arranged such that the cover spring exerts an opening force both onto the first and onto the second cover part.

2. The apparatus according to claim 1, wherein the first retainer is integral with the first cover part.

3. The apparatus according to claim 1, wherein the first cover part comprises a first hinge part and the housing comprises a second hinge part, the first and second hinge parts forming a hinge to pivotally connect the first cover part to the housing and the hinge comprising a clearance fit between the first and second hinge parts, and the cover part biasing mechanism is configured to exert the biasing force onto the first cover part in the closed position to bias the first hinge part inwardly and/or distally against the second hinge part.

4. The apparatus according to claim 1, wherein the cover latch is configured for locking the first cover part in the closed position, the cover latch being moveable relative to the first cover part between a locked position and an unlocked position, wherein the cover latch at least partially forms the cover part biasing mechanism.

5. The apparatus according to claim 4, wherein the first cover part comprises a locking extension with a locking head for interacting with the cover latch in the closed position of the first cover part, the locking head comprising a first end configured to interact with an inclined surface of the cover latch in such a way that in the closed position of the first cover part and in the locked position of the cover latch, the locking head is biased inwardly and/or distally against the housing.

6. The apparatus according to claim 5, wherein the locking head comprises a second end configured to interact with an inclined surface of the housing in such a way that in the closed position of the first cover part and in the locked position of the cover latch, the first cover part is biased inwardly and/or distally against the housing.

7. The apparatus according to claim 5, wherein the apparatus comprises a cover close switch for detecting whether the first cover part is in the closed position, the cover close switch being arranged to be activated by the locking head in the closed position of the first cover part.

8. The apparatus according to claim 1, wherein the first retainer comprises a cartridge reference face for aligning the first cartridge within the first retainer and the apparatus further comprises a cartridge biasing mechanism for exerting a biasing force onto the first cartridge in the first retainer to bias the first cartridge against the cartridge reference face.

9. The apparatus according to claim 8, wherein the cartridge biasing mechanism is separate from the cover part biasing mechanism.

10. The apparatus according to claim 8, wherein the apparatus comprises a piston rod for expelling a substance from the first cartridge within the first retainer and a cartridge bias sleeve slidably disposed over the piston rod, the cartridge bias sleeve being biased towards the cartridge reference face by a sleeve bias mechanism.

11. The apparatus according to claim 10, wherein the piston rod comprises a protruding lip on an end of the piston rod facing the first retainer and the cartridge bias sleeve comprises a corresponding rabbet on an end of the cartridge bias sleeve facing the first retainer.

12. The apparatus according to claim 10, wherein the cover latch is slidably disposed adjacent to the cartridge bias sleeve, wherein the cover latch comprises a keyway extending partway along the cover latch, the keyway engaging a corresponding lug provided on the cartridge bias sleeve.

13. The apparatus according to claim 1, wherein the first cover part comprises an outer side wall covering the first retainer from an outside, the outer side wall having resilient properties against a compressive force imposed from the outside.

14. The apparatus according to claim 1, wherein the apparatus is configured such that the first cover part or the second cover part is moveable to the open position only if the respective other cover part is in the closed position.

15. The apparatus according to claim 1, wherein the apparatus is a medicament delivery device.

16. The apparatus according to claim 1, wherein the apparatus is hand-held.

17. The apparatus of claim 1, wherein the cover part biasing mechanism comprises a spring configured to exert the biasing force.

18. A drug delivery device comprising:
a housing, a first retainer holding a first cartridge containing a pharmaceutically active compound and a second retainer holding a second cartridge containing a pharmaceutically active compound, a first cover part for accessing the first retainer and a second cover part for accessing the second retainer, the first and second cover parts being moveable relative to the housing between an open position and a closed position, a cover part biasing mechanism configured to exert a biasing force onto the first cover part in the closed position to bias the first cover part inwardly and/or distally against the housing, the cover part biasing mechanism comprising a cover latch being moveable relative to the first cover part, the cover latch configured to be deflected by the first cover part in the closed position, wherein deflection of the cover latch by the first cover part exerts the biasing force onto the first cover part, and a cover spring arranged such that the cover spring exerts an opening force both onto the first cover part and onto the second cover part.

* * * * *